United States Patent
Tompkins et al.

(10) Patent No.: US 11,918,223 B2
(45) Date of Patent: Mar. 5, 2024

(54) SUTURELESS GRAFT ANASTOMOTIC QUICK CONNECT SYSTEM

(71) Applicant: University of Louisville Research Foundation, Inc., Louisville, KY (US)

(72) Inventors: Landon H. Tompkins, Louisville, KY (US); Michael Sobieski, Floyds Knobs, IN (US); Steven Koenig, Floyds Knobs, IN (US); Gretel Monreal, Louisville, KY (US); Mark Slaughter, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 530 days.

(21) Appl. No.: 16/963,789

(22) PCT Filed: Feb. 1, 2019

(86) PCT No.: PCT/US2019/016285
§ 371 (c)(1),
(2) Date: Jul. 21, 2020

(87) PCT Pub. No.: WO2019/152799
PCT Pub. Date: Aug. 8, 2019

(65) Prior Publication Data
US 2021/0052272 A1 Feb. 25, 2021

Related U.S. Application Data

(60) Provisional application No. 62/625,635, filed on Feb. 2, 2018.

(51) Int. Cl.
*A61B 17/11* (2006.01)
(52) U.S. Cl.
CPC ....... *A61B 17/11* (2013.01); *A61B 2017/1107* (2013.01); *A61B 2017/1121* (2013.01); *A61B 2017/1135* (2013.01)

(58) Field of Classification Search
CPC ............ A61B 17/11; A61B 2017/1121; A61B 2017/1135; A61B 2017/1107
See application file for complete search history.

(56) References Cited

U.S. PATENT DOCUMENTS 4,182,339 A * 1/1980 Hardy, Jr. ........... A61B 17/1114
606/154
5,827,316 A 10/1998 Kanner et al.
(Continued)

OTHER PUBLICATIONS

Notification of Transmittal of The International Search Report and The Written Opinion of the International Searching Authority for International Application No. PCT/US2019/016285, entitled "Sutureless Graft Anastomotic Quick Connect System," dated May 20, 2019.
(Continued)

*Primary Examiner* — Jing Rui Ou
(74) *Attorney, Agent, or Firm* — Hamilton, Brook, Smith & Reynolds, P.C.

(57) ABSTRACT

Disclosed are devices and methods for providing simple, fast, effective, and repeatable anastomotic graft connections, which can reduce (or eliminate) risks associated with graft anastomoses, thus improving patient outcomes. An example embodiment is an anastomotic graft connection device that includes a connector and a cuff. The connector includes a first flared end and a second flared end. The first flared end is configured to be inserted into a vessel (e.g., blood vessel). At least the second flared end is configured to be attached to a graft. The cuff includes an inner ring and an outer ring. The inner ring is configured to secure the graft to at least the second flared end of the connector, and the outer ring is configured to exert force on the vessel to seal the first flared end of the connector against an inner wall of the vessel.

22 Claims, 11 Drawing Sheets

(56) References Cited

U.S. PATENT DOCUMENTS

| | | |
|---|---|---|
| 6,030,395 A | 2/2000 | Nash et al. |
| 6,117,147 A | 9/2000 | Simpson et al. |
| 6,398,797 B2 | 6/2002 | Bombard et al. |
| 6,602,263 B1 | 8/2003 | Swanson et al. |
| 6,616,675 B1 * | 9/2003 | Evard .................. A61F 2/2493 606/155 |
| 6,682,540 B1 | 1/2004 | Sancoff et al. |
| 6,776,785 B1 | 8/2004 | Yencho et al. |
| 6,972,023 B2 | 12/2005 | Whayne et al. |
| 7,303,569 B2 | 12/2007 | Yencho et al. |
| 7,585,306 B2 | 9/2009 | Abbott et al. |
| 8,162,963 B2 | 4/2012 | Abbott |
| 8,777,971 B2 | 7/2014 | Tulleken et al. |
| 9,023,377 B2 | 5/2015 | Nugent et al. |
| 10,159,485 B2 * | 12/2018 | Asfora .................. A61B 17/11 |
| 2003/0187499 A1 | 10/2003 | Swanson et al. |
| 2005/0149073 A1 | 7/2005 | Arani et al. |
| 2005/0192604 A1 * | 9/2005 | Carson ................ A61F 2/2493 606/153 |
| 2007/0123917 A1 * | 5/2007 | Ortiz .................. A61B 17/1114 606/153 |
| 2007/0249985 A1 * | 10/2007 | Brenneman .......... A61B 17/083 604/890.1 |
| 2008/0015617 A1 | 1/2008 | Harari et al. |
| 2008/0249546 A1 | 10/2008 | Sandstrom et al. |
| 2009/0054970 A1 * | 2/2009 | Houser .............. A61B 17/0644 623/1.36 |
| 2011/0118765 A1 | 5/2011 | Aguirre |
| 2011/0172761 A1 | 7/2011 | Barker |
| 2012/0123453 A1 | 5/2012 | Asfora et al. |
| 2014/0180314 A1 * | 6/2014 | Asfora .................. A61B 17/04 606/155 |
| 2015/0313598 A1 * | 11/2015 | Todd ........................ A61F 2/90 606/153 |
| 2015/0313599 A1 * | 11/2015 | Johnson ........... A61B 17/12022 606/191 |

OTHER PUBLICATIONS

International Preliminary Report on Patentability for International Application No. PCT/US2019/016285 entitled "Sutureless Graft Anastomotic Quick Connect System" dated Aug. 4, 2020.

* cited by examiner

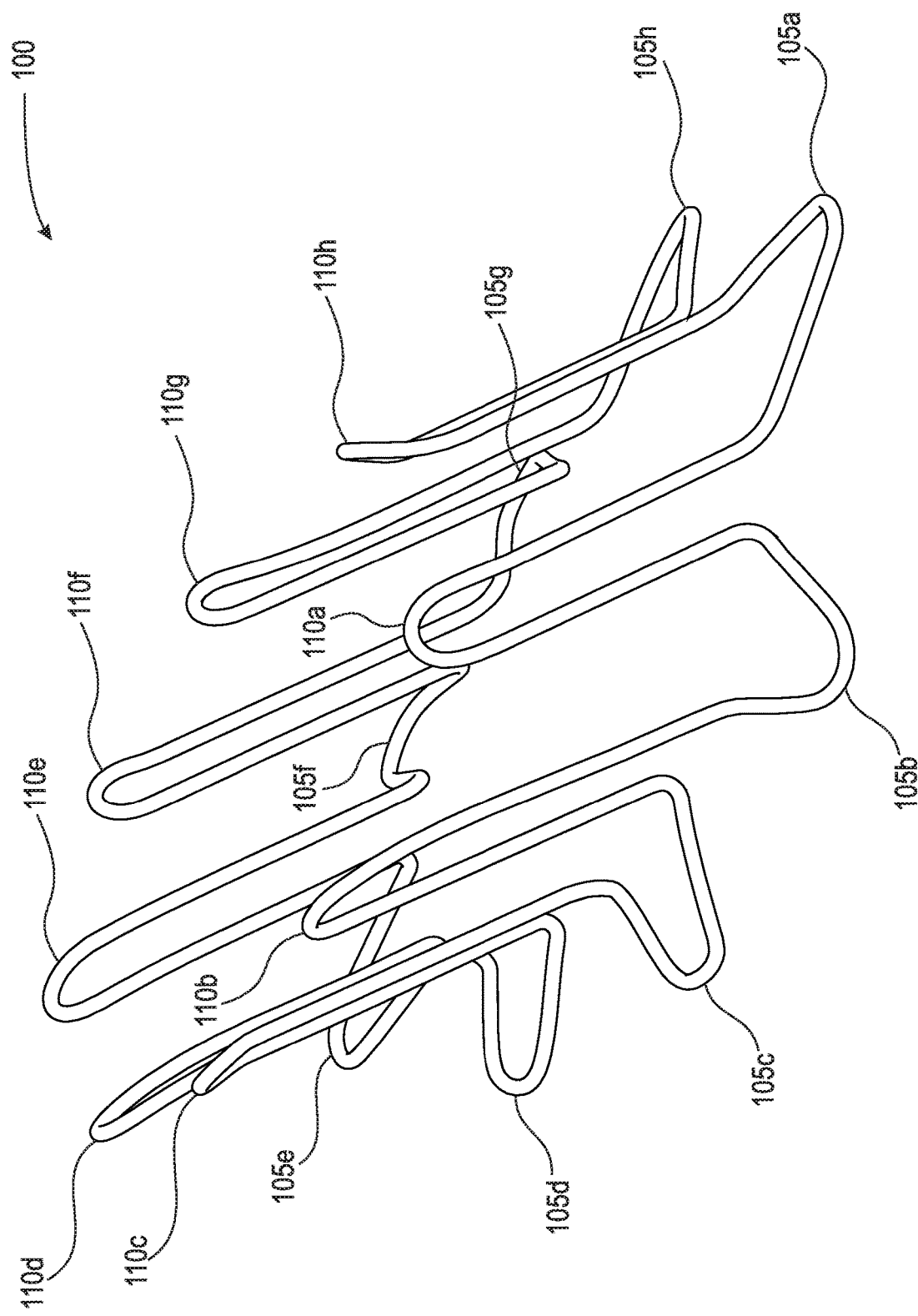

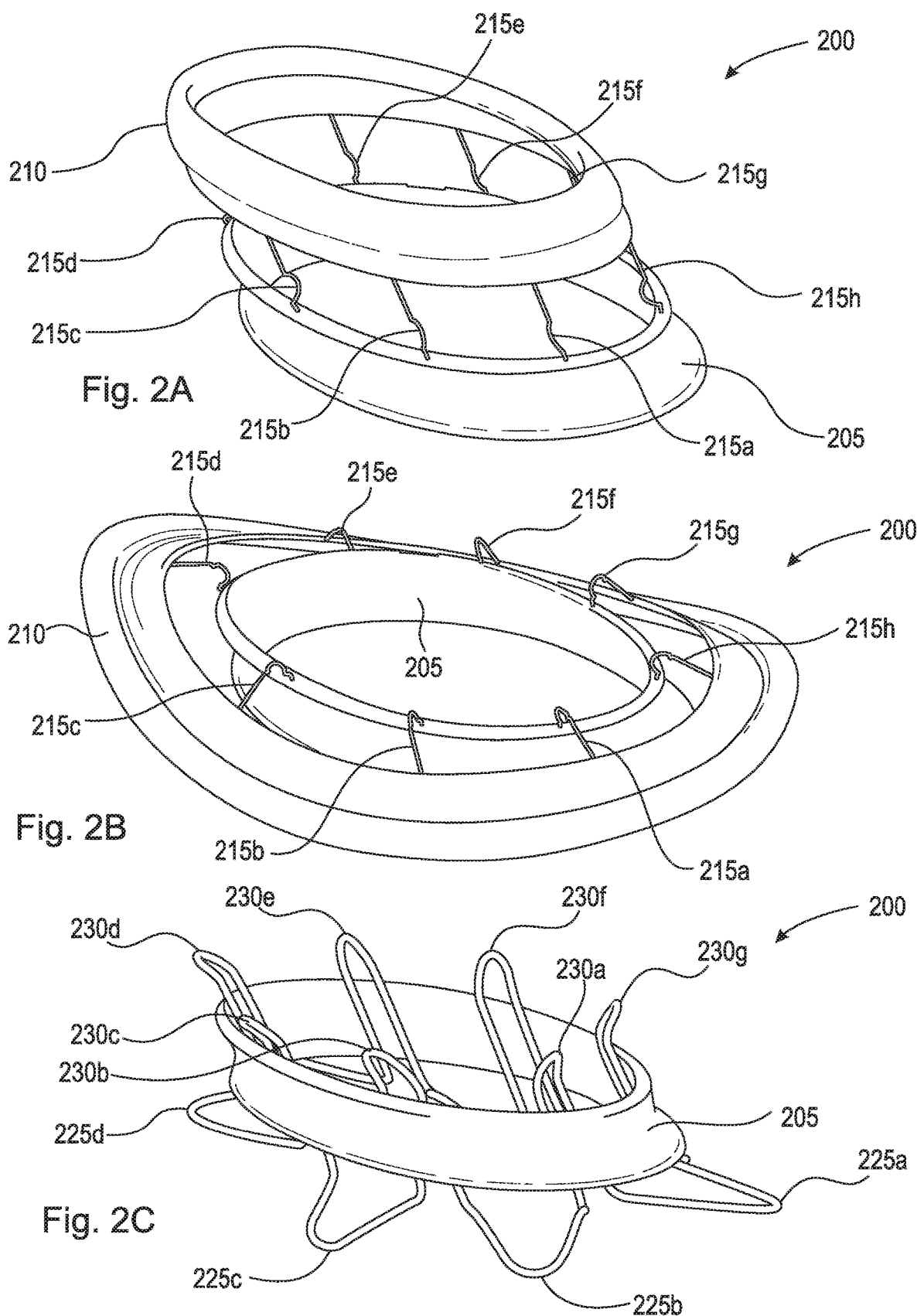

SUTURELESS GRAFT ANASTOMOTIC QUICK CONNECT SYSTEM

RELATED APPLICATION(S)

This application is the U.S. National Stage of International Application No. PCT/US2019/016285, filed on Feb. 1, 2019, which designates the U.S., published in English, and claims the benefit of U.S. Provisional Application No. 62/625,635, filed on Feb. 2, 2018. The entire teachings of the above application(s) are incorporated herein by reference.

BACKGROUND

Implantation procedures for clinically-approved mechanical circulatory support (MCS) devices are invasive, time consuming, prone to adverse events, and often require a median sternotomy, cardiopulmonary bypass (CPB), and partial clamping (cross-clamping) of the aorta to facilitate anastomosis of the outflow graft. Median sternotomy and CPB, however, are associated with adverse events including risk of post-operative infection, bleeding, and pulmonary complications. Further, aortic clamping may be associated with post-operative neurological complications and potential aortic dissection. Conventional manual suturing techniques are currently used to attach an outflow graft to the aorta. CPB support and aortic clamping time may also increase risk of post-operative adverse events.

SUMMARY

The disclosed devices and methods reduce (or eliminate) these risks and improve patient outcomes by providing simple, fast, effective, and repeatable solutions for graft anastomosis. An example embodiment is an anastomotic graft connection device that includes a connector and a cuff. The connector includes a first flared end and a second flared end. The first flared end is configured to be inserted into a vessel (e.g., an aorta or other blood vessel). At least the second flared end is configured to be attached to a graft. The cuff includes an inner ring and an outer ring. The inner ring is configured to secure the graft to at least the second flared end of the connector, and the outer ring is configured to exert force on the vessel to seal the first flared end of the connector against an inner wall of the vessel.

Another example embodiment is an anastomotic graft connection device that includes a continuous wire forming a first flared end, a second flared end, and pillars between the first flared end and the second flared end. The first flared end is configured to be inserted into a vessel, and at least the second flared end is configured to be attached to a graft.

In the above embodiments, the inner ring and outer ring can be connected by a plurality of elastic members. The elastic members can be made of nitinol wires, for example. The inner ring and the outer ring can be made of silicone, for example. The connector can be made of nitinol wire, for example. The first flared end and the second flared end can each include a plurality of wings. For example, the first flared end can include eight wings and the second flared end can include eight wings. Pillars between the first flared end and the second flared end can be angled at, for example, forty to seventy degrees with respect to the vessel in which the device is to be inserted.

Another example embodiment is an anastomotic graft connector deployment tool. The example tool includes an outer housing, an inner shaft configured to retain an anastomotic graft connector, a coring member arranged inside the inner shaft, and a handle coupled to the outer housing and the inner shaft. The handle is operable to advance or retract the inner shaft with respect to the outer housing. The tool further includes a coring actuator configured to deploy the coring member and a releasing actuator configured to release the anastomotic graft connector. The outer housing and the inner shaft of the deployment tool can include interfacing threaded portions, and the handle can be configured to rotate to cause the interfacing threaded portions to rotate with respect to each other to advance or retract the inner shaft with respect to the outer housing. The inner shaft can include a plurality of retractable hooks operatively coupled to the releasing actuator to retain the anastomotic graft connector until released by the releasing actuator. While the anastomotic graft connector is retained in the deployment tool, the connector can be in a deformed state. The coring member can include a circular plate and blade operatively coupled to the coring actuator. The coring actuator and releasing actuator can include buttons coupled to the outer housing. A graft can be secured to a flared end of the anastomotic graft connector and inserted into the deployment tool for delivery with the anastomotic graft connector.

Another example embodiment is a method of connecting a graft to a vessel (e.g., blood vessel). The example method includes coring a vessel and inserting a first flared end of an anastomotic graft connector into the vessel. A graft is secured to at least a second flared end of the anastomotic graft connector by an inner ring of a cuff, thus the graft is also inserted into the vessel along with the first flared end of the connector. The method further includes releasing an outer ring of the cuff to exert force on the vessel to seal the first flared end of the anastomotic graft connector against an inner wall of the vessel. A deployment tool having the anastomotic graft connector and the graft installed in the deployment tool may be used to connect the graft to the vessel. Coring the vessel can includes using a coring member of the deployment tool. Inserting the first flared end of the anastomotic graft connector into the vessel can include rotating a handle of the deployment tool to advance an inner shaft of the deployment tool. The anastomotic graft connector can be retained by the inner shaft. Releasing the outer ring of the cuff can include further rotating the handle to further advance the inner shaft and expose the outer ring of the cuff.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIGS. 1A-1E illustrate an anastomotic graft connection device, according to an example embodiment. FIG. 1A shows a perspective view, FIG. 1B shows a front elevation view, FIG. 1C shows a side elevation view, FIG. 1D shows a top view, and FIG. 1E shows a bottom view.

FIGS. 2A-2B illustrate a cuff for use with an anastomotic graft connection device, according to an example embodiment.

FIG. 2C illustrates a ring of a cuff applied to an anastomotic graft connection device.

DETAILED DESCRIPTION

Figure 1B:
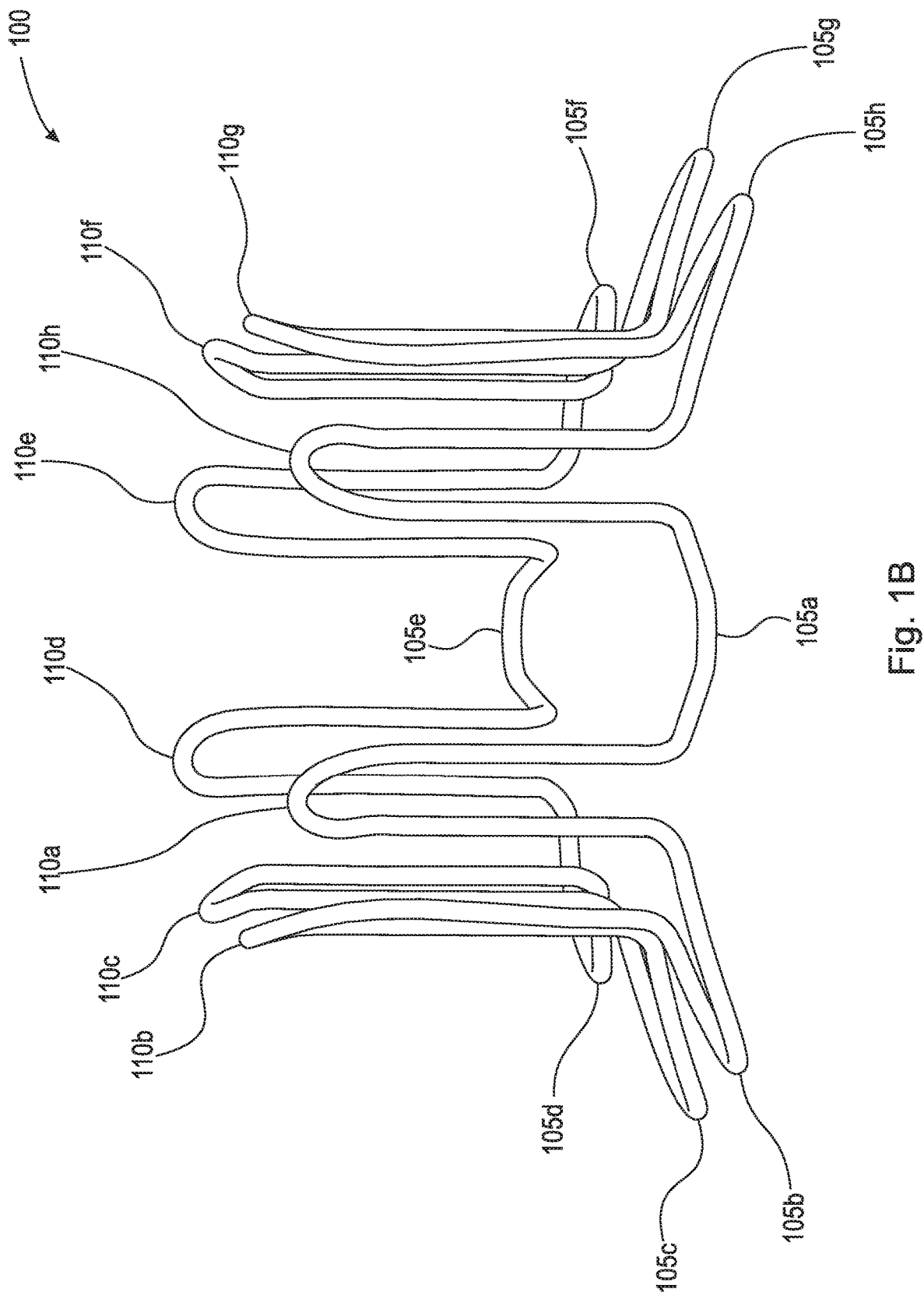
Figure 1C:
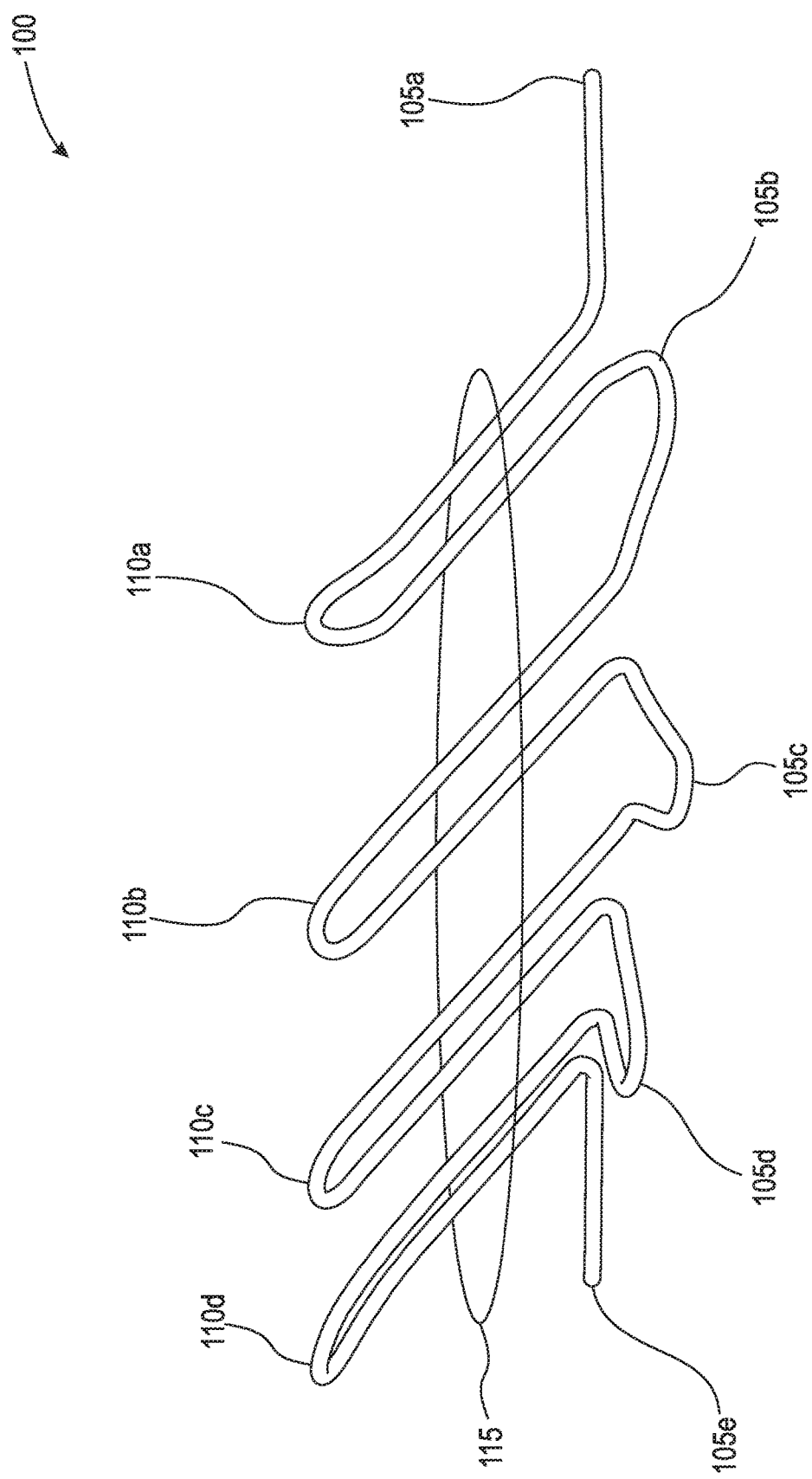
Figure 1D:
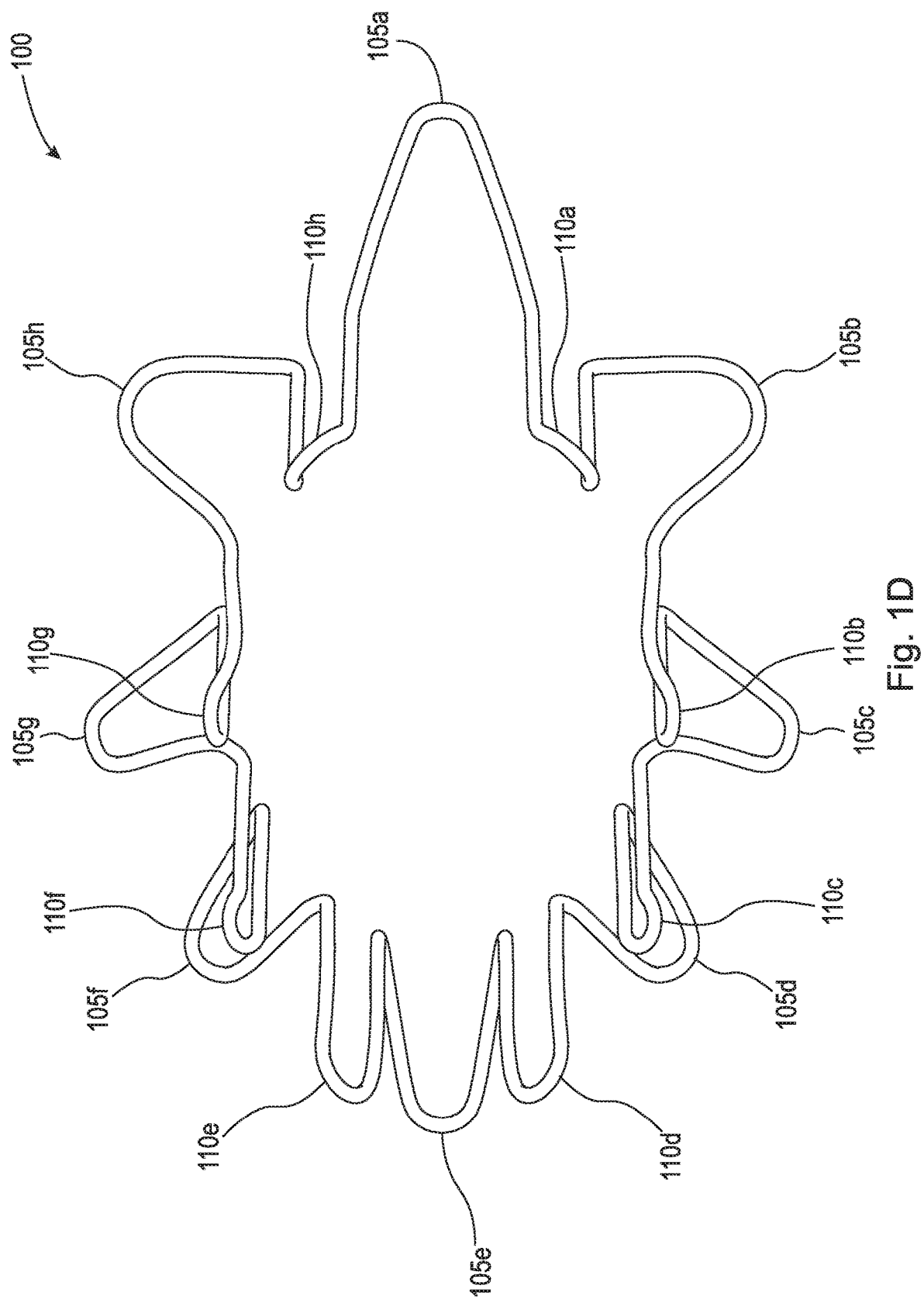
Figure 1E:
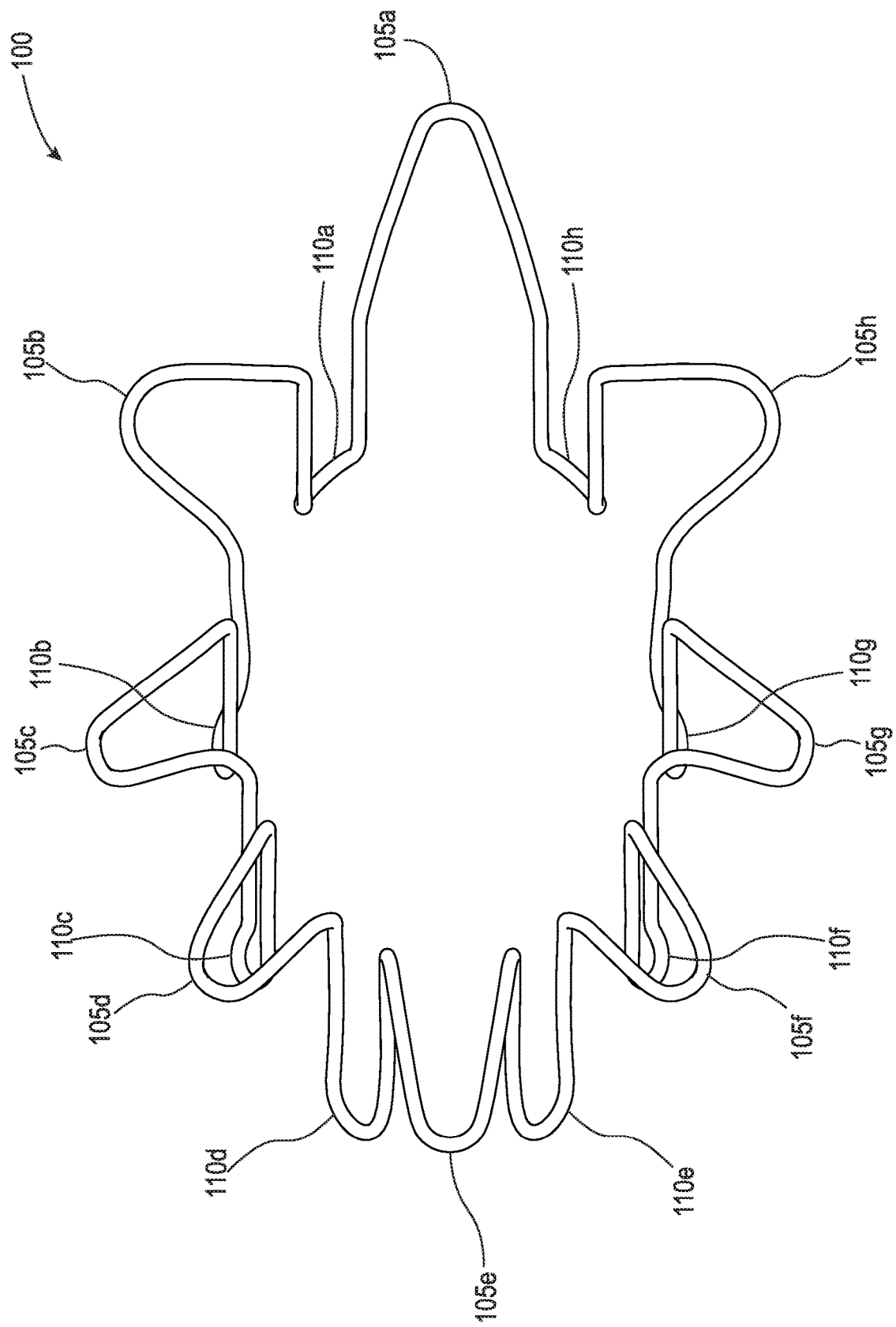

A description of example embodiments follows.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the relevant art.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the disclosed embodiments as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a," "an," and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter is based, at least in part, on the development of a sutureless anastomotic graft connection device to eliminate manual suturing of vascular grafts to a patient's vessels (e.g., aorta or other large diameter blood vessels). One initial indication for use will enable sutureless connection of the outflow graft of a left ventricular assist device (LVAD), or other mechanical circulatory support (MCS) device, to the aorta. The connection device provides an end-to-side anastomosis connection for vascular grafts to native vessels. End-to-side anastomosis is the surgical connection of a tubular graft end to the side of a native blood vessel, enabling blood flow through the graft and into the native vessel. Additional embodiments include an integrated cutting (aortotomy) and deployment tool as well as automating the delivery of the device, which allows novel, minimally-invasive implantation procedure(s) that should further reduce operation time and improve patient outcomes.

An example embodiment of a device is unique in that it can be designed to attach large diameter grafts (10-15 mm diameter) to large blood vessels (18-28 mm diameter) using a hybrid polymer-mechanical seal to achieve hemostasis. An example device is a nitinol winged connector attached to the distal end of a graft and an external polymer-flanged cuff that covers the end-to-side intersection of the aortotomy and graft. The super-elastic properties of annealed nitinol allow for the winged connector to be deformed and compressed for loading into a deployment-aortotomy tool, and restored to its functional shape when delivered, enabling distal graft anastomosis via a less-invasive surgical approach.

FIGS. 1A-1E illustrate an anastomotic graft connection device 100, according to an example embodiment. The device 100 includes a continuous wire forming a first flared end (collectively 105a-h), a second flared end (collectively 110a-h), and pillars 115 between the first flared end 105a-h and the second flared end 110a-h. The first flared end 105a-h is configured to be inserted into a vessel, and at least the second flared end 110a-h is configured to be attached to a graft. The device can be made of nitinol wire, for example, or any other suitable elastic material. The first flared end and the second flared end can each include a plurality of wings. For example, the first flared end can include eight wings 105a-h and the second flared end can include eight wings 110a-h. Pillars 115 between the first flared end and the second flared end can be angled at, for example, about forty to seventy degrees with respect to the vessel in which the connection device 100 is to be inserted.

In the case of a connection device made from nitinol (also referred to herein as a "nitinol anchor"), in one example embodiment, the device includes a collapsible nitinol anchor (0.36 mm dia. NiTi #1-SE, Light Oxide) that provides sutureless anchoring of the graft to the aorta wall. The anchor enables hemostatic sealing under elevated pressure conditions, possesses equivalent pull out strength compared to current attachment strategies (i.e., traditional suturing), and reduces anastomosis time and incision size. Although nitinol anchors have been used to anchor grafts perpendicular (90° angle) to coronary arteries, the embodiments disclosed herein are novel in at least that they can be applied to anchor a large vessel (aorta) to a large graft (10-15 mm diameter) at a 40° angle (to minimize turbulent flow) while also providing a hemostatic seal. The example anchor is comprised of eight securing flanges, or "wings," 105a-h that deploy inside the aorta and act as mechanical anchors. Vertical pillars 115 extend from the nitinol ring base approximately 1 5mm and at a 40° take-off angle to better fit the beveled outflow graft. The sutureless anchor approach should reduce access time by minimum of 10 minutes, reduce incision size by 4 cm, and provide stability equivalent or greater pullout strength compared to suture anastomosis (feasibility testing completed). Additionally, the connection device 100 may eliminate the need for CPB and cross-clamping of the aorta, shortening surgery time, and may also reduce intraoperative transfusion requirements.

Nitinol is an appropriate material to construct the collapsible anchor, however, other materials may also be used. For example, spring steel may be used as it has similar superelastic properties and overall strength (alloy), which are the primary design criteria. Similarly, an elastic polymer with hardness and strength that meet design criteria may also be used.

FIGS. 2A and 2B illustrate a cuff 200 for use with an anastomotic graft connection device, according to an example embodiment. The cuff 200 (also referred to herein as an "external mounting ring") can include in an example embodiment, a silicone rubber (or elastic polymer) ring 205 used externally to secure a graft to the vertical pillars 115 of the nitinol winged anchor 100. The elastic external mounting ring 200 can contain two parts, an inner ring 205 that circumferentially attaches a graft to the nitinol vertical pillars 115 (like a rubber band) and an outer ring 210 that applies downward force to externally seal the connection between the connection device 100 and the aorta. When a graft is attached to the connection device 100 such that the graft at least partially covers the first flared end 105a-h, the connection of the device 100 to the aorta seals the graft with the aorta. The outer ring 210 can be attached to the inner ring 205 with several nitinol arms 215a-h. The nitinol arms 215a-h can be annealed into a shape such that the arms 215a-h force downward pressure, as shown in FIG. 2B. Once the device 100 is in place inside the aorta, the external ring's nitinol arms 215a-h can be released to snap downward, anchoring the device 100 (internally and externally) to the vessel wall. The nitinol anchor's wings 105a-h provide internal support and anchoring while the outer ring 210 of the mounting ring 200 provides external support.

For loading of a graft onto the device 100, once a surgeon has sized and trimmed the graft to length, the graft can be mounted to the device 100. The end of the graft to be mounted can be cut at the desired take-off angle (e.g., 40 degrees). The cut beveled end of the graft can be flared and slid over the vertical pillars 115 of the nitinol anchor 100. Flaring of the graft end can allow the graft to partially cover the wings 105a-h of the anchor 100. The external elastic mounting ring 200 is then stretched open and slid around the outside of the graft. The mounting ring 200 is then released, the internal ring 205 closes around the graft and the vertical pillars 115 of the nitinol anchor, securely attaching the graft to the anchor 100. The flared portion of the graft can also be pushed down onto the wings 105a-h of the anchor 100 by the external mounting ring 200.

FIG. 2C illustrates a ring 205 of a cuff applied to an anastomotic graft connection device 220. Connection device 220 is another example configuration of an anastomotic graft connection device and differs from connection device 100 in that connection device 220 includes seven wings of its first flared end, four of which 225a-d can be seen in FIG. 2C, and seven wings 230a-g of its second flared end.

Figure 3A:
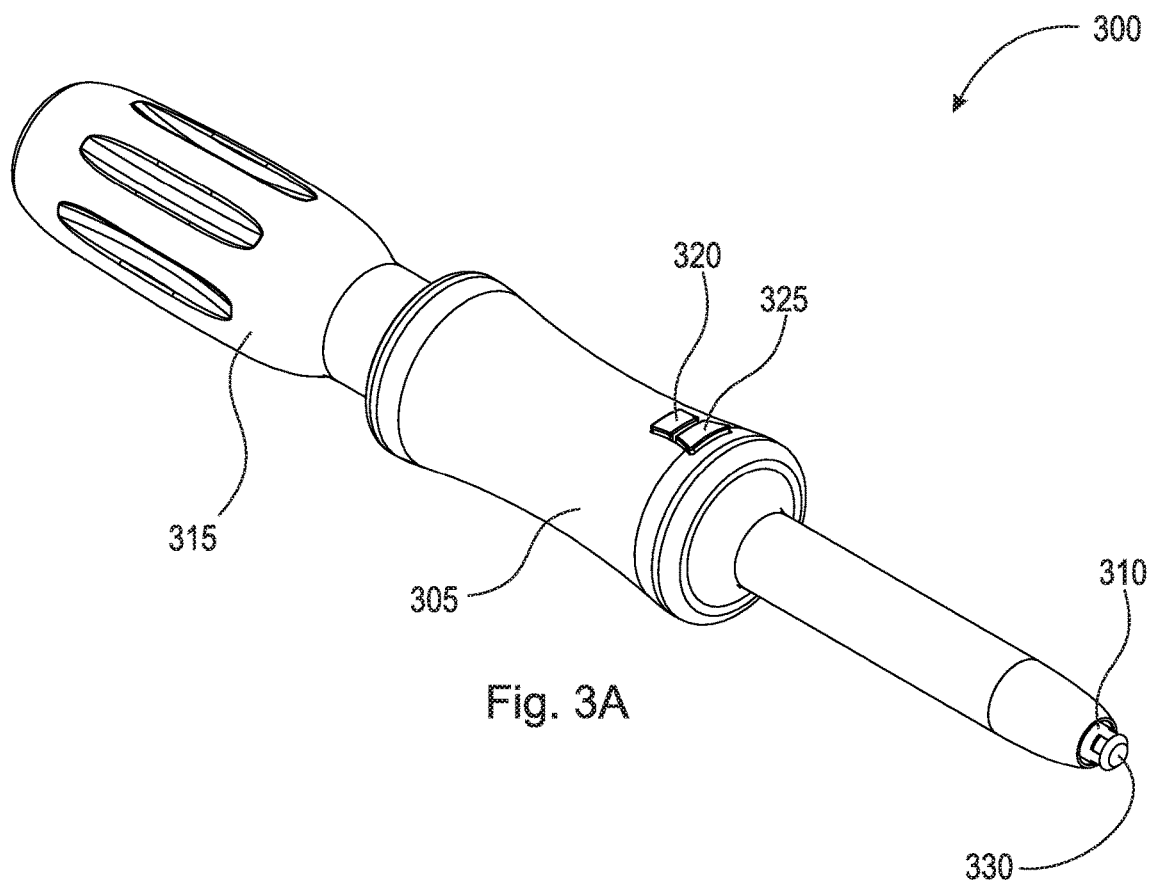
FIGS. 3A and 3B illustrate a deployment tool for an anastomotic graft connection device, according to an example embodiment.
Figure 3B:
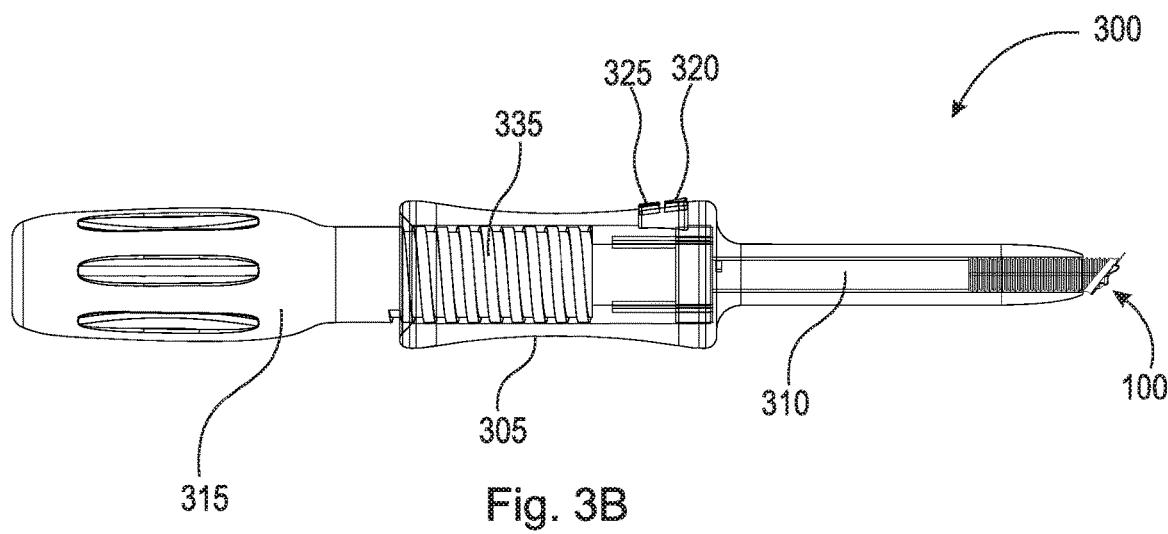

FIGS. 3A and 3B illustrate a deployment tool 300 for an anastomotic graft connection device (e.g., connection device 100), according to an example embodiment. The example deployment tool 300 can include an outer housing 305, a threaded delivery handle 315, an inter-lumen shaft 310 that connects to the delivery handle 315, and a coring aortotomy cutting tool 330 in the interior of the inter-lumen shaft 310. The outer housing 305 can include two buttons 320 and 325, one for deploying the coring cutting tool 330, and the other for releasing the device 100 from the inter-lumen shaft 310. The threaded handle 315 can advance and retract the inter-lumen shaft 310 to expose or capture the device 100 into the outer housing sheath 305.

Figure 3C:
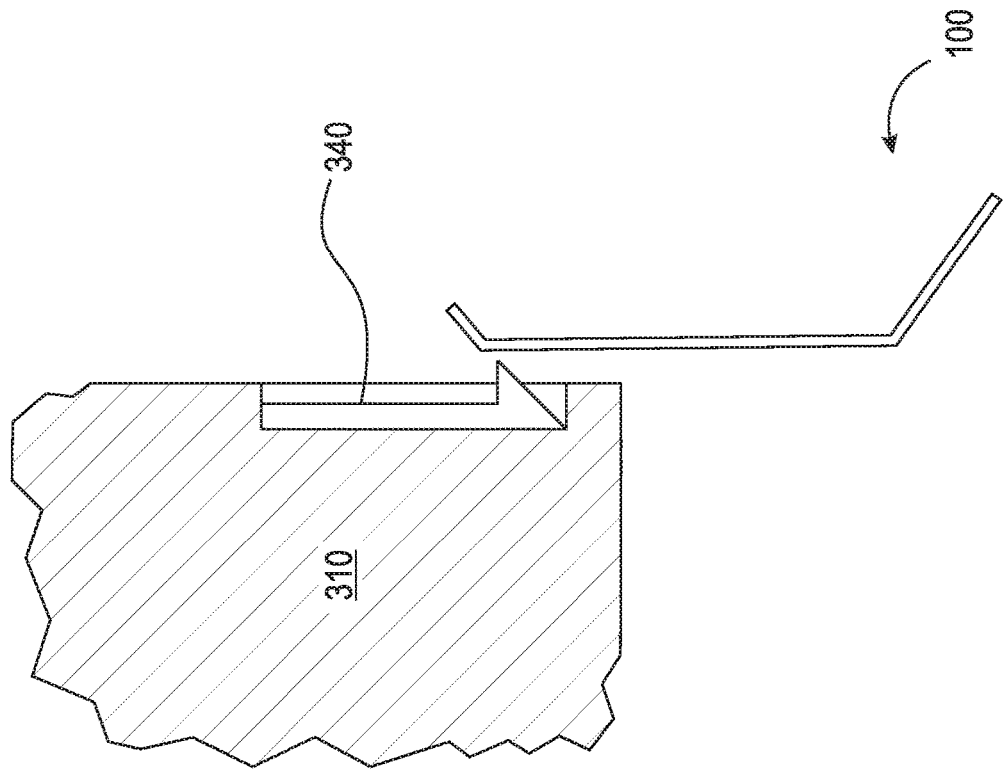
FIGS. 3C and 3D illustrate one of a plurality of retractable hooks for retaining an anastomotic graft connector in the deployment tool of FIGS. 3A and 3B, according to an example embodiment.
Figure 3D:
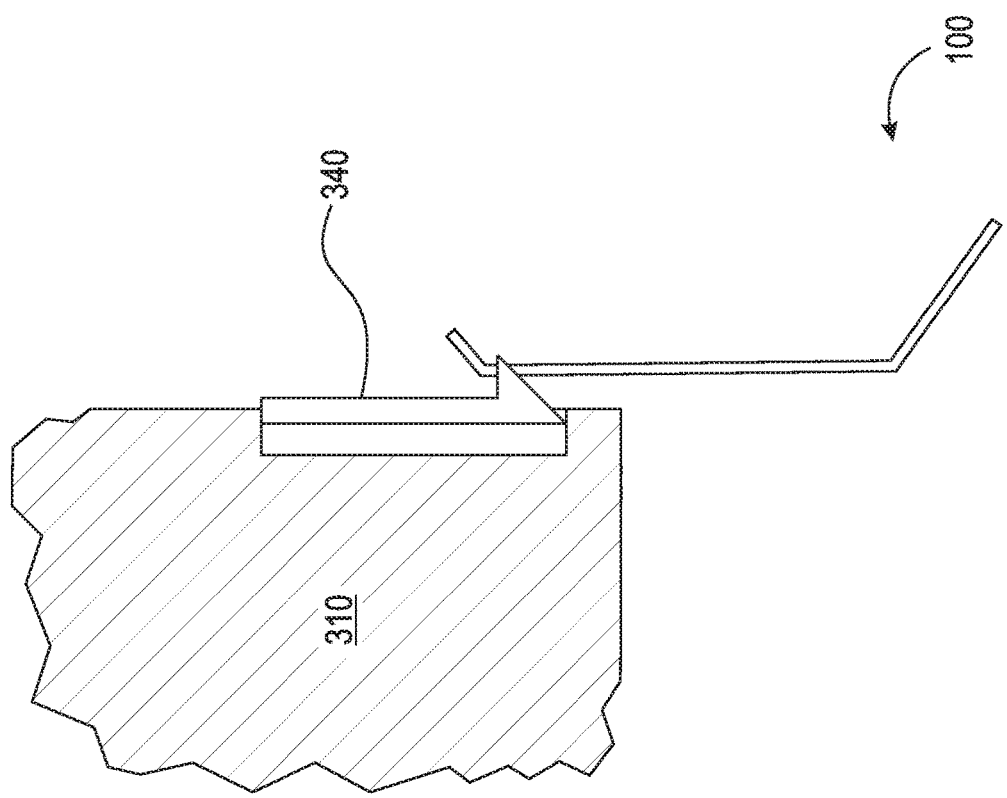

FIGS. 3C and 3D illustrate one 340 of a plurality of retractable hooks for retaining a connection device 100 in the deployment tool 300 of FIGS. 3A and 3B, according to an example embodiment. A plurality of hooks, one of which is shown as 340, can be integrated around the circumference of the inter-lumen shaft 310 of the deployment tool 300. To retain the connection device 100 in the deployment tool 300, the hooks can extend from the shaft 310 and through the upper flared ends 110a-h of the connection device. Only one hook 340 and only a portion of the connection device 100 is shown in FIGS. 3C and 3D for simplicity. The hooks can be spring loaded and can retract back inside the shaft 310 to disengage from the connection device 100. A button, for example, on the housing 305 of the tool 300 can be used to actuate the hooks to retract into the shaft 310.

Figure 4:
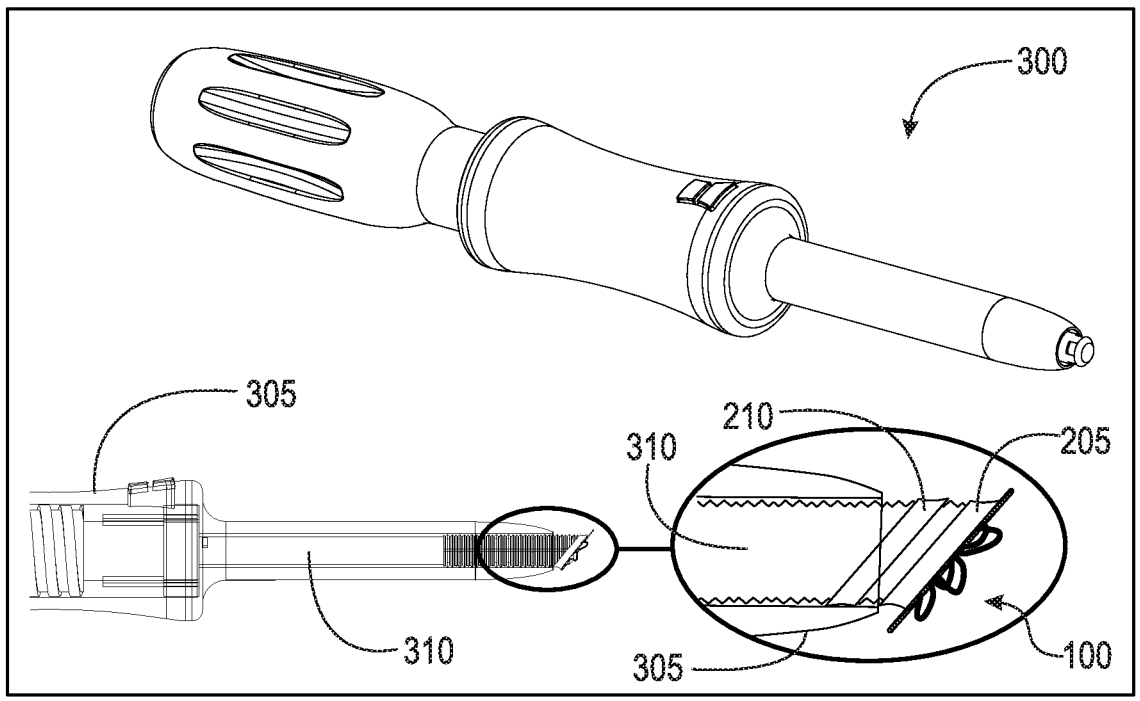
FIG. 4 illustrates an anastomotic graft connection device installed in the deployment tool of FIG. 3A, according to an example embodiment.

FIG. 4 illustrates an anastomotic graft connection device 100 installed in a deployment tool 300, according to an example embodiment. To load a device/graft assembly onto the deployment tool 300, the device 100 (nitinol anchor and outflow graft) can be pre-loaded onto the inter-lumen portion, e.g., shaft 310, of the deployment tool 300, which enables rapid and controlled delivery into a cored vessel. The inter-lumen shaft 310 may contain multiple, retractable hooks that attach interiorly to the vertical pillars 115 or upper wings 110*a-h* of the nitinol anchor 100 or other mounting mechanism(s) to secure the device 100 to the inter-lumen shaft 310. Within the inter-lumen portion of the deployment tool 300 can be a circular coring tool 330 used for making the aortotomy. The inter-lumen shaft 310 may be detachable from the deployment tool housing 305 for easy mounting of the device 100 and can then be reattached to the deployment tool housing 305 for device delivery. Once reattached to the deployment tool housing 305 the inter-lumen shaft 310 can be retracted into the deployment tool sheath 305 using the threaded handle 315, enabling the collapse of the nitinol wings 105*a-h*.

FIGS. 5A-5D illustrate delivering an anastomotic graft connection device from a deployment tool, according to an example embodiment. To deliver a device/graft assembly into a vessel (e.g., aorta), initially, this procedure can be performed with the aorta cross clamped, to isolate the section where the anastomosis will occur and reduce the amount of blood loss during the coring of the vessel. A balloon system may be employed to aid in a bloodless delivery of connection device 100 and to eliminate the need for cross clamping. A site on the ascending aorta, for example, is identified for outflow graft placement, cross clamped, and a small incision can be made with a scalpel blade. The incision will allow for the insertion of the distal tip of the coring tool 330. The distal tip of the coring tool 330 (part of the deployment device) can be inserted into the aorta through the previously made incision. This distal tip can be a circular plate supported by a shaft that runs through the center of the tool 300. The plate extends into the vessel through the incision and, when retracted, pulls the vessel wall up to a circular cutting knife of the coring tool 330. The distal tip can also twist when retracting to allow for a circular cutting motion. The tip also captures the cored piece of tissue and retracts it into the coring knife to clear the area for device insertion. This mechanism may be similar to other mechanisms common in vessel coring tools, such as the Quest Medical (Allen, Tex.) CleanCut aortotomy tool.

Figure 5A:
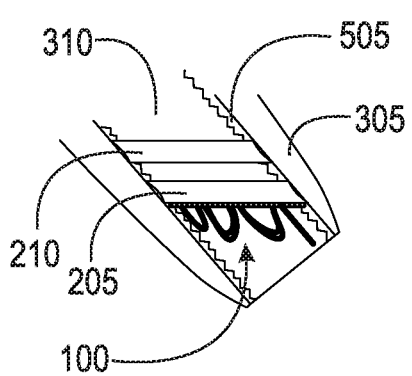
FIGS. 5A-5D illustrate delivering an anastomotic graft connection device from a deployment tool, according to an example embodiment.
Figure 5B:
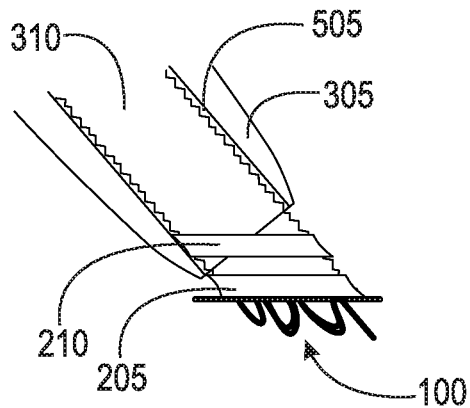
Figure 5C:
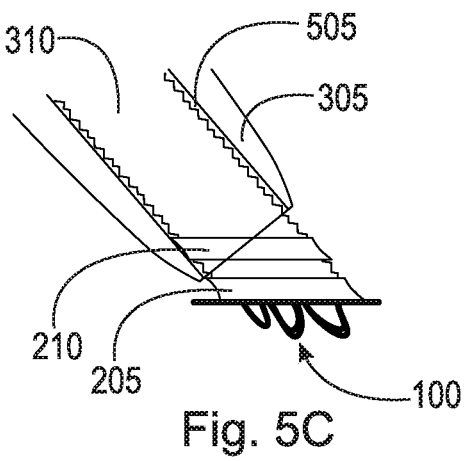
Figure 5D:
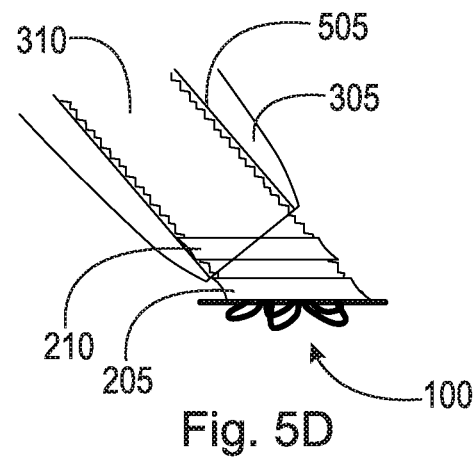

Once the aorta has been cored, the coring tool 330 is retracted internally inside the deployment tool 300. The proximal handle portion 315 of the deployment tool 300 has a threaded deployment mechanism 335 to improve control of device delivery. Once the tip of the delivery sheath is appropriately placed in the cored portion of the aorta, the connector device 100 can be advanced into the aorta by turning (threading) the handle 315. A mechanism allows the winged connector 100 to be deployed in steps to insure a successful seal. With reference to FIG. 5A, the device 100 is advanced out of the housing 305 and into the cored aorta. With reference to FIG. 5B, the rear wing 105*e* (heel) of the nitinol anchor 100 is deployed first. This allows a surgeon to confirm that the anchor 100 is inside the true lumen of the aorta. With reference to FIG. 5C, once confirmed, the front wing 105*a* (toe) of the anchor 100 is then deployed. With reference to FIG. 5D, the remaining side wings of the anchor are deployed, completely anchoring the device 100 to the aorta.

After the nitinol winged anchor 100 has been fully deployed and secured into place, the inter-lumen shaft 310 can continue to advance and the housing 305 of the deployment tool retracts. Once the housing 305 is retracted enough to fully expose the external mounting ring 200, arms of the mounting ring will deploy, applying external pressure and sealing on the exterior wall of the aorta. Because the graft 505 is attached to the connection device 100 such that the graft at least partially covers the first flared end 105*a-h*, the connection of the device 100 to the aorta seals the graft 505 with the aorta. Once the external ring 200 is fully deployed and complete hemostasis has been achieved, the deployment tool 300 can be retracted and removed, leaving the connection device 100 and attached graft 505 in place. The free end of the graft can be clamped to avoid blood loss until the surgeon is ready to attach the graft.

Figure 6:
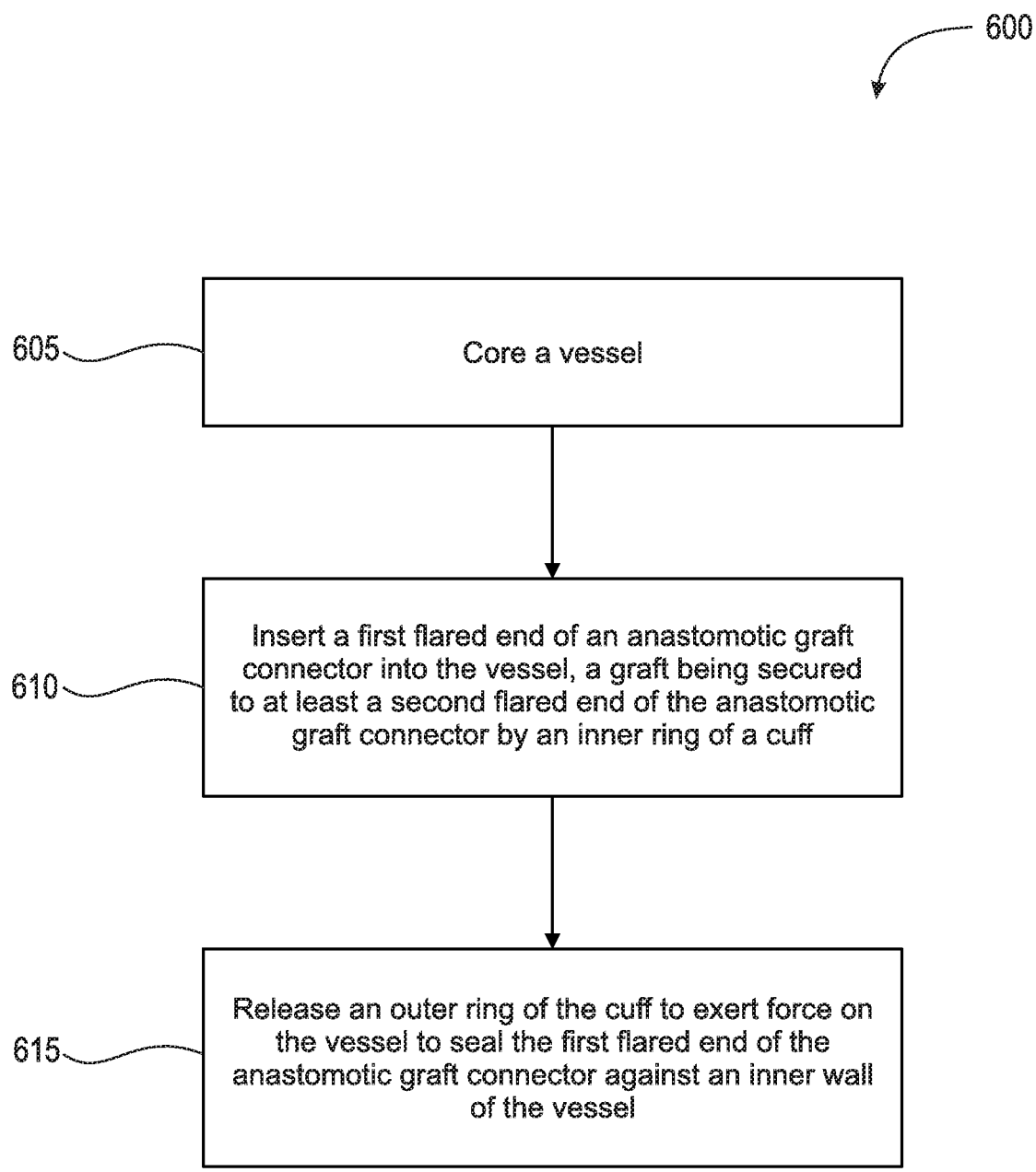
FIG. 6 illustrates a method of connecting a graft to a vessel, according to an example embodiment.

FIG. 6 illustrates a method 600 of connecting a graft to a vessel, according to an example embodiment. The example method includes coring 605 a vessel and inserting 610 a first flared end of an anastomotic graft connector into the vessel. A graft is secured to at least a second flared end of the anastomotic graft connector by an inner ring of a cuff, thus the graft is also inserted into the vessel along with the first flared end of the connector. The method further includes releasing 615 an outer ring of the cuff to exert force on the vessel to seal the first flared end of the anastomotic graft connector against an inner wall of the vessel.

Figure 7A:
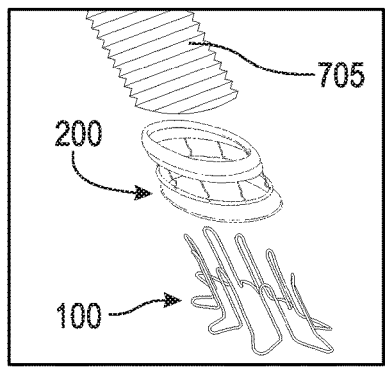
FIGS. 7A-7E illustrate an anastomotic graft connection device attached to a vessel, according to an example embodiment.
Figure 7B:
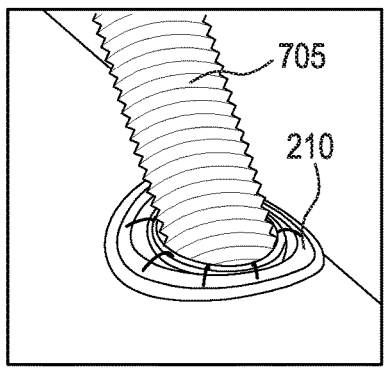
Figure 7C:
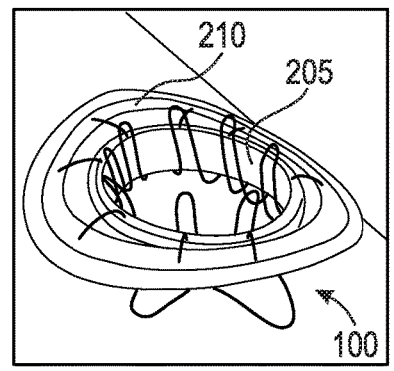
Figure 7D:
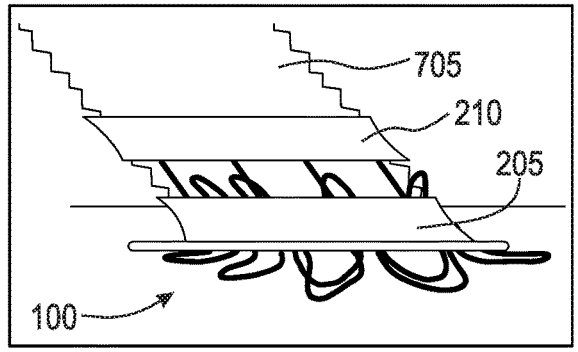
Figure 7E:
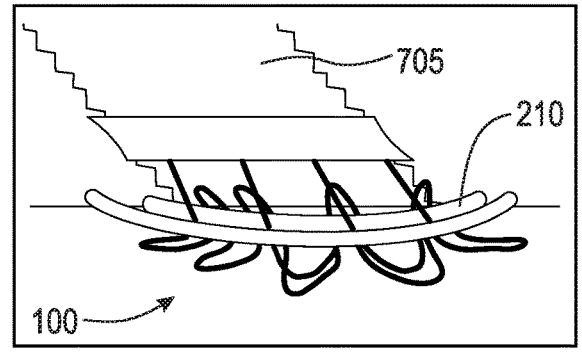

FIGS. 7A-7E illustrate an anastomotic graft connection device attached to a vessel, according to an example embodiment. FIG. 7A illustrates the connection device 100, external cuff 200, and example graft 705. The graft may be an artificial graft or a natural vessel grafted from a body. FIG. 7B illustrates the connection device 100, external cuff 200, and graft 705 attached to a vessel (e.g., blood vessel). FIG. 7C illustrates the connection device 100 and external cuff 200 (without showing the graft 705) attached to a vessel. FIG. 7D illustrates from a side view the connection device 100, external cuff 200, and graft 705 inserted into a vessel before deployment of the outer ring 210. FIG. 7E illustrates from a side view the connection device 100, external cuff 200, and graft 705 attached to a vessel.

The foregoing description includes details regarding the fabrication of the connection device 100, cuff 200, and deployment tool 300, and demonstrate feasibility as evidenced by a secure, sutureless, and leak-free (hemostatic seal) connection to the aorta. However, and without being bound by any particular theory or mechanism, there are many other applications for the embodiments disclosed herein, including a smaller diameter axillary or subclavian graft to serve as a vascular access ports for dialysis, chemotherapy, and MCS support devices. In some embodiments, the immediate application of the connection device 100 would be to allow for a fast and simple, sutureless anastomosis of grafts to blood vessels (e.g., an aorta) or other vessels, such as a urethra. In some embodiments, the device can allow a sutureless graft anastomosis without the need for cardiopulmonary bypass and aortic cross-clamping achieved by coupling the device with an integrated cutting (aortotomy) and deployment tool. The device could be adapted for end-to-side anastomosis of any tubular graft of any diameter to a hollow organ allowing blood (or other fluid) flow. The device could be adapted for minimally-invasive, laparoscopic, endoscopic, and/or natural orifice transluminal endoscopic surgeries. The device could be adapted into a small diameter axillary or subclavian vascular access port to facilitate the introduction of intra-aortic balloon pumps and other MCS devices intended to be placed within the aorta. The device may be refined to provide vascular access for dialysis and chemotherapy. Additionally, it is believed that the presently-disclosed subject matter allows fast, repeatable, and effective sutureless connection of grafts to the aorta, and could eliminate the need for CPB and aortic cross-clamping during implantation. Moreover, automating the delivery of the device could lead to novel, minimally-invasive implantation procedures. The device could also allow angled anastomosis that may promote favorable flow patterns to minimize blood clot formation and reduce blood stagnancy areas, and the system components can be easily down- or up-scaled to allow for anastomosis between various vascular graft and native vessel diameters.

While example embodiments have been particularly shown and described, it will be understood by those skilled in the art that various changes in form and details may be made therein without departing from the scope of the embodiments encompassed by the appended claims.

What is claimed is:

1. An anastomotic graft connection device, the device comprising:
   a connector including a first flared end and a second flared end, the first flared end configured to be inserted into a vessel, and at least the second flared end configured to be attached to a graft, the first flared end and the second flared end including a plurality of wings; and
   a cuff including an inner ring and an outer ring spaced from the inner ring, the inner ring and outer ring connected by a plurality of elastic members, the inner ring configured to secure the graft to at least the second flared end of the connector, and the outer ring configured to exert force on the vessel to seal the first flared end of the connector against an inner wall of the vessel.

2. The anastomotic graft connection device of claim 1 wherein the plurality of elastic members includes nitinol wires.

3. The anastomotic graft connection device of claim 1 wherein the connector includes a continuous wire forming the first flared end, the second flared end, and pillars between the first flared end and the second flared end.

4. The anastomotic graft connection device of claim 3 wherein the wire is a nitinol wire.

5. The anastomotic graft connection device of claim 1 wherein the first flared end includes eight wings and the second flared end includes eight wings.

6. The anastomotic graft connection device of claim 1 wherein the inner ring and the outer ring are silicone rings.

7. The anastomotic graft connection device of claim 1 wherein the connector is configured to connect the graft to the vessel at an angle between forty and seventy degrees.

8. A method of connecting a graft to a vessel, the method comprising:
   coring a vessel;
   inserting the anastomotic graft connection device of claim 1, comprising inserting the first flared end of the connector into the vessel, a graft being secured to at least the second flared end of the connector by the inner ring of the cuff; and
   releasing the outer ring of the cuff to exert force on the vessel to seal the first flared end of the connector against an inner wall of the vessel.

9. The method of claim 8 wherein connecting the graft to the vessel includes using a deployment tool having the connector and the graft installed in the deployment tool, and wherein coring the vessel includes using a coring member of the deployment tool.

10. The method of claim 9 wherein inserting the first flared end of the connector into the vessel includes rotating a handle of the deployment tool to advance an inner shaft of the deployment tool, the connector being retained by the inner shaft.

11. The method of claim 10 wherein releasing the outer ring of the cuff includes further rotating the handle to further advance the inner shaft and expose the outer ring of the cuff.

12. The anastomotic graft connection device of claim 1 wherein inner ring is a band configured to circumferentially attach the graft to the connector.

13. The anastomotic graft connection device of claim 1 wherein the outer ring is movable relative to the inner ring from a position apart from the first flared end to a position adjacent the first flared end.

14. The anastomotic graft connection device of claim 13 wherein the outer ring, when in the position adjacent the first flared end, at least partially encircles the inner ring.

15. An anastomotic graft connection device, the device comprising:
   a continuous wire forming a first flared end, a second flared end, and pillars between the first flared end and the second flared end, the first flared end configured to be inserted into a vessel, and at least the second flared end configured to be attached to a graft, the pillars being angled to enable the wire to connect the graft to the vessel at an angle between forty and seventy degrees; and
   a cuff including an inner ring and an outer ring, the inner ring and outer ring connected by a plurality of elastic members, the inner ring configured to secure the graft to at least the second flared end, and the outer ring configured to exert force on the vessel to seal the first flared end against an inner wall of the vessel.

16. The anastomotic graft connection device of claim 15 wherein the first flared end and the second flared end include a plurality of wings.

17. The anastomotic graft connection device of claim 16 wherein the first flared end includes eight wings and the second flared end includes eight wings.

18. The anastomotic graft connection device of claim 15 wherein inner ring is a band configured to circumferentially attach the graft to the pillars.

19. The anastomotic graft connection device of claim 15 wherein the outer ring is movable relative to the inner ring from a position apart from the first flared end to a position adjacent the first flared end.

20. The anastomotic graft connection device of claim 19 wherein the outer ring, when in the position adjacent the first flared end, at least partially encircles the inner ring.

21. An anastomotic graft connection device, the device comprising:
   a continuous wire forming a first flared end, a second flared end, and pillars between the first flared end and the second flared end, the first flared end configured to be inserted into a vessel, and at least the second flared end configured to be attached to a graft, the pillars being angled to enable the wire to connect the graft to the vessel at an angle between forty and seventy degrees; and
   a cuff including an inner ring and an outer ring, the outer ring being movable relative to the inner ring from a position apart from the first flared end to a position adjacent the first flared end, the inner ring configured to secure the graft to at least the second flared end, and the outer ring configured to exert force on the vessel to seal the first flared end against an inner wall of the vessel.

22. The anastomotic graft connection device of claim 21 wherein the outer ring, when in the position adjacent the first flared end, at least partially encircles the inner ring.

* * * * *